(12) United States Patent
Petitjean

(10) Patent No.: US 9,173,834 B2
(45) Date of Patent: Nov. 3, 2015

(54) REGENERATION COMPOSITION AND METHOD FOR NATURAL HAIR RECOLORATION AND STIMULATION OF HAIR GROWTH BY PROCESSED MAKROOT FRUIT EXTRACT

(76) Inventor: Max W. Petitjean, Tokyo (JP)

( * ) Notice: Subject to any disclaimer, the term of this patent is extended or adjusted under 35 U.S.C. 154(b) by 0 days.

(21) Appl. No.: 14/395,882

(22) PCT Filed: Apr. 26, 2012

(86) PCT No.: PCT/EP2012/001785
§ 371 (c)(1),
(2), (4) Date: Jan. 27, 2015

(87) PCT Pub. No.: WO2013/159790
PCT Pub. Date: Oct. 31, 2013

(65) Prior Publication Data
US 2015/0150783 A1    Jun. 4, 2015

(51) Int. Cl.
| | | |
|---|---|---|
| *A61K 36/00* | (2006.01) | |
| *A61K 36/752* | (2006.01) | |
| *A61K 8/97* | (2006.01) | |
| *A61Q 5/10* | (2006.01) | |
| *A61Q 7/00* | (2006.01) | |
| *A61Q 5/00* | (2006.01) | |

(52) U.S. Cl.
CPC .................. *A61K 8/97* (2013.01); *A61K 36/752* (2013.01); *A61Q 5/00* (2013.01); *A61Q 5/10* (2013.01); *A61Q 7/00* (2013.01)

(58) Field of Classification Search
None
See application file for complete search history.

(56) References Cited

FOREIGN PATENT DOCUMENTS

| JP | 7126129 A | 5/1995 |
|---|---|---|
| JP | 2001031528 A | 2/2001 |
| JP | 2004083416 A | 3/2004 |
| JP | 2007270134 A | * 10/2007 |

OTHER PUBLICATIONS

Written Opinion issued in connection with PCT/EP2012/001785.

* cited by examiner

*Primary Examiner* — Qiuwen Mi
(74) *Attorney, Agent, or Firm* — Berliner & Associates

(57) ABSTRACT

The invention refers to a natural hair re-coloration and hair growth composition comprising boiled Makroot fruit (*Citrus hystrix* DC Rutaceae) that when applied returns white or grey hair to its original color and causes newly re-grown hair to return to its original color as well. The composition also stimulates hair growth. It is composed of natural organic ingredients and thus the composition is low cost and easy to prepare and the application of the composition is quite simple.

7 Claims, 2 Drawing Sheets

Figure 1. Examples 1-11

Figure 2:
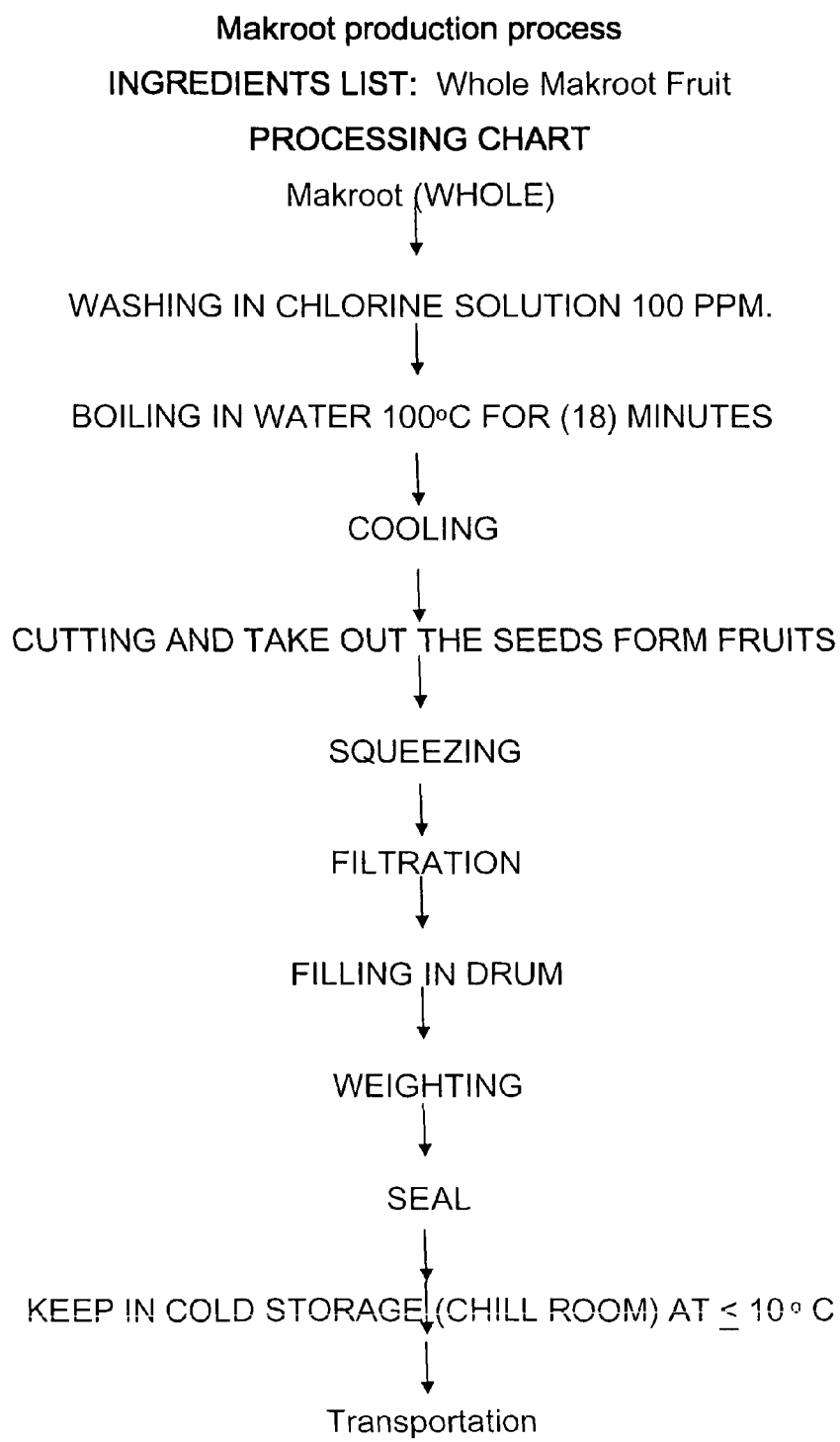

| No. | Sex | Age | Start using | During using (weeks) | Frequency (time/week) | Result | Week of resulted | How Darker | How Itching | How Falling | How Dandruff |
|---|---|---|---|---|---|---|---|---|---|---|---|
| 1 | Female | 35 | Aug-10 | 2 | 2,3 | Yes | 2 | 1 | - | - | 1 |
| 2 | Female | 27 | Apr-10 | 4+ | 2,3 | Yes | 2 | 1 | 1 | 1 | 1 |
| 3 | Female | 40 | Aug-10 | 4 | 1 | Yes | 4 | - | 1 | - | - |
| 4 | Female | 31 | Aug-10 | 4 | 2,3 | Yes | 3 | - | 1 | 1 | 1 |
| 5 | Male | 45 | Aug-10 | 4 | 1 | Yes | 4 | 1 | 1 | 1 | 1 |
| 6 | Female | 39 | Jul-10 | 4+ | 2,3 | Yes | 4 | - | - | 1 | 1 |
| 7 | Female | 36 | Aug-10 | 3 | 2,3 | Yes | 2 | 1 | 1 | 1 | - |
| 8 | Female | 40 | Jul-10 | 4 | 4,5 | Yes | 3 | - | - | - | - |
| 9 | Female | 41 | Aug-10 | 3 | 2,3 | Yes | 2 | - | 1 | 1 | 1 |
| 10 | Female | 40 | Aug-10 | 3 | 2,3 | Yes | 2 | 1 | 1 | - | - |
| 11 | Female | 40 | Jun-10 | 4+ | 2,3 | Yes | 3 | - | 1 | - | - |

| No. | Side Effect | Recommend to Friends | Comments |
|---|---|---|---|
| 1 | No | Yes | Wants to see the new generation to use it. |
| 2 | No | Yes | Hairs are darkers and feels a bit straighter hairs. |
| 3 | No | Yes | Stronger hairs. |
| 4 | No | Yes | No hairs fall and dandruff |
| 5 | No | Yes | Demands to be placed in market many and soon. |
| 6 | No | Yes | Lowers dandruff and hairs fall |
| 7 | No | Yes | - |
| 8 | No | Yes | Hairs are darker. |
| 9 | No | Yes | Lowers itch and shining hairs. |
| 10 | No | Yes | Lowers itch and fall. |
| 11 | No | Yes | Demands other products from Ma-Krood |

| | |
|---|---|
| Total Questionnairs: | 11 |
| There are female: | 91% |
| Average age: | 38 |
| Can see result | 100% |
| Average weeks of result: | 3 |
| Darker hairs: | 55% |
| Itching: | 73% |
| Falling: | 55% |
| Dandruff: | 55% |
| No Side Effect: | 100% |
| Recommend to Friends: | 100% |

Flow Chart of the Process of Preparing the NHR Composition

REGENERATION COMPOSITION AND METHOD FOR NATURAL HAIR RECOLORATION AND STIMULATION OF HAIR GROWTH BY PROCESSED MAKROOT FRUIT EXTRACT

TECHNICAL FIELD

The present invention relates to a natural hair recoloration and hair growth stimulation composition (hereinafter referred to as "NHR composition") and a method for naturally recoloring and stimulating hair growth (hereinafter to referred to as "NHR method"), and, more particularly to a composition for use in the natural recoloration of hair and natural stimulation of hair growth and a method for naturally recoloring hair and stimulating new hair growth in its original color, used for white hair appearing on the head.

Up until the present time, the development of compositions for use on the hair such as tonic or hair growth stimulant and hair recoloration agents and the like has been promoted vigorously due to the desire to control or eliminate hair loss and to return white or grey hair to its original color. Among these kinds of hair use compositions, when developing hair recoloration agents, it is important to elucidate the mechanism for the generation of grey or white hair and research to discover that mechanism has been carried out.

It has become clear that grey or white hair is generated primarily by the failure of melanin pigment which is produced in pigment cells to be incorporated into the hair shaft. There are several explanations for the cause and to date, the fundamental underlying reason why these pigment cells cease producing sufficient melanin to maintain hair color has not been identified. Moreover, until now, with regard to hair recoloration products having the effect of blackening white hair, although laid open Japanese Patent Application 2010-031056 Patent, incorporated by reference and made a part hereof, discloses the anticipated achievement of this effect by means of a composition containing extracts of several natural products, in fact the effectiveness of that composition is extremely limited, and the results of its application range between no effect and failing to adequately recolor white or grey hair. To date essentially no effective agent for the natural recoloration of hair has been proposed.

SUMMARY OF THE PRESENT INVENTION

A significant relationship between the stress a person experiences and changes in hair coloration is known to exist, and, especially in light of the probability of a person experiencing stress in a variety of social environments, the introduction of a natural hair recoloration use composition that is low cost and can be used easily in addition to effectively returning white hair to its original color, is greatly desirable.

The objective of the present invention is to offer a composition for natural hair recoloration that makes it possible to return white hair to its original color, stimulates the hair growth, is low cost and can be used easily.

Means of Solving the Problem

To achieve the aforestated objective, the NHR composition of the present invention is characterized in that it contains an extract obtained from a Makroot fruit that has been boiled, typically in water or aqueous solution. Preferably, the aforestated extract is applied directly to the pertinent hair growth site.

Moreover, to achieve the aforestated purpose, the NHR method of the present invention is characterized in that it returns white hair in the aforestated sites of hair growth sites to its original color and stimulates hair growth, by rubbing the boiled Makroot fruit, the extracts thereof or a composition of its extract on one or more occasions onto the said hair growth sites.

According to the present invention, when the NHR composition is applied to the hair growth sites, because it contains extracts obtained from the boiled Makroot fruit, the white hair in the said hair growth sites will return to its original color and hair growth is stimulated through the action of the said extracts on the said hair growth sites. No expensive ingredients or chemical additives or complex apparatuses or procedures are required and application may even be done by hand. Therefore, together with it being possible to effectively return white hair to its original color and stimulate hair growth, the NHR composition of the present invention is low cost and it is possible to use it simply.

Moreover, according to the present invention, because the cut surface of the Makroot fruit is rubbed onto the hair growth sites one or more times, the white hairs in these hair growth sites and new growing hair return to their original color. Therefore, together with the effective return of white hair to its original color, the NHR method is low cost and possible to apply very simply.

SIMPLE EXPLANATION OF THE DRAWINGS

FIG. 1. This Figure shows the experimental conditions and results of practice examples consisting of experiments carried out using the NHR composition and the NHR method of the present invention that demonstrate the form of the present invention.

FIG. 2. This Figure shows the detailed preparation of the NHR composition and the subsequent steps of its application in the NHR method.

DETAILED DESCRIPTION OF THE PRESENT INVENTION

The inventor of the present invention as a result of earnest study for the purpose of achieving the aforementioned objective, has discovered a revolutionary NHR composition and NHR method. That is to say, from among the many existing natural products that could be applied to natural hair recoloration and hair growth stimulation, he selected citrus fruits, and from among citrus fruits he selected the Makroot fruit, and by using the extract in various forms of the said Makroot fruit found he was able to effectively return white hair to its original color and stimulate hair growth when he applied the extract or compositions containing the extract to hair growth sites. Moreover, by directly using the low priced Makroot fruit, he found that it is possible to return white hair to its original color and stimulate hair growth at a low cost, and it can be used easily without complex treatments or processes.

The present invention was prepared based on the results of the aforestated research. Following is a detailed description of the NHR composition and method and an explanation of the form of the practice of the present invention. The NHR composition and NHR method of the present invention have been developed in response to the present state of the art, and, in particular, in response to the problems and needs in the art that have not yet been fully solved by currently available hair recoloration compositions and methods for inexpensively returning hair to its original color. Thus it is an overall objective of the present invention to provide a method for natural hair recoloration that achieves significant improvement in recoloration of white or grey hair, stimulates the hair growth and reduces costs and difficulty of application by the user.

The purpose of the NHR composition and NHR method is to allow the consistent natural recoloration and hair growth stimulation of hair at a high degree of effectiveness and a significantly higher degree of simplicity and at the same time lower cost.

Through application of the NHR composition and NHR method of the present invention, the consistent results of a significantly more effective recoloration of grey or white hair and hair growth stimulation with lower expense or difficulty has been achieved.

All dimensions in the present invention are based on a Makroot fruit diameter of about 5 centimeters and a boiling vessel volume of about 5 liters and may be altered as needed in proportion to changes in the size or other characteristics of the Makroot fruit used and the volume of the boiling vessel used. The specific dimensions given herein are in no way limiting but are by way of example to demonstrate an effective embodiment of the invention. For the avoidance of doubt, dimensions include, without limitation, dimensions of parts, flow rates, measurement of volume, time periods, concentrations and temperatures.

The Makroot fruit used in the present invention (Makroot Fruit) (Scientific name *Citrus histrix* DC Rutaceae or *Citrus×hystrix*, Japanese name "Kobu Mikan") is known by such names as "Kaffir Lime", "Kieffer Lime" or "Limau Purut" (hereinafter it shall be referred to simply as "Makroot"), and is one variety of citrus produced in South East Asia in countries such as Indonesia or Malaysia. Historically, it has been used widely as a natural ingredient in Chinese traditional medicine, in spices for cooking and in bathing salts and the like.

The inventor of the present invention has found an effect completely different from the effects in the existing application of Makroot mentioned above. That is to say, he discovered that when he applied the extracts obtained from the boiled Makroot to the hair growth sites of the head and jaw, white hair returned to its original color and hair re-grew in its original color and hair growth was stimulated. As an application method, for example, an extremely easy method may be used whereby Makroot fruits that could easily be obtained at a low price are boiled and then sectioned into several pieces of desired or convenient size, and the sectioned surfaces of the divided Makroot are rubbed on the hair growth sites and the like one or more times.

The Makroot fruit of the present invention is not particularly limited but any fruit of the species *Citrus histrix* DC Rutaceae may be used. The degree of ripeness of the Makroot fruit that can be used in the present invention is not particularly limited and any fruit that has grown to within 4 weeks of full ripeness may be used, but Makroot fruit within one week of full ripeness or later is preferred and fully ripe Makroot fruit is more preferred. The period for which Makroot fruit that has fully ripened and been left on the tree or picked may be used is not limited but Makroot fruit within three months of full ripeness is preferred, and Makroot fruit within one month of full ripeness is more preferred. The size of the Makroot fruit to be used is not particularly limited and any size of Makroot fruit may be used as the Makroot fruit of the present invention, but fruits having a diameter of between 3 and 6 centimeters are preferred. The degree of exposure to sunlight is also not limited and any ripened or almost ripened Makroot fruit may be used but Makroot fruit well exposed to sunlight is preferred.

The Makroot fruit of the present invention is boiled prior to use or extraction. This creates a more effective NHR composition that shows more striking results when used comparably with the unboiled NHR composition or the present invention. It is believed that this occurs because the components effective in bringing about the recoloration of white hair are present in considerable quantities in the rind. Boiling of the whole fruit forces these components to migrate to the pulp of the fruit where they may be used or extracted far more effectively than from the rind. Although boiling refers to a phase transition in which a liquid reaches the gas phase, for purposes of the present invention, the term boiling shall also include steeping the Makroot fruit in water or an aqueous solution or suspension at temperatures at or above 95° C. Makroot fruit steeped in such water, aqueous solution or suspension shall be considered to be "boiled Makroot fruit" for the purposes of the present invention. Though boiling is convenient in that it maintains a steady temperature for the treatment of the Makroot fruit, the actual vaporization of water or other components of the solution or suspension are not essential to the preparation of the boiled Makroot fruit of the present invention.

The method of boiling the Makroot fruit of the present invention is not particularly limited. The liquid in which the Makroot fruit is boiled may be any natural aqueous solution or suspension, brine or water itself and water is preferred. The temperature of boiling is not particularly limited but it is preferred to be between 85° C. and 180° C., more preferred to be between 95° C. and 130° C. and even more preferred to be between 100° C. and 110° C. If the boiling is at too low a temperature, the desired effect of migration of constituents from the rind to the pulp does not occur. If it is too high, degradation of the natural compounds may occur. Boiling may be carried out under open atmosphere or in a pressurized vessel. In the latter case the pressure applied is not particularly limited but may be as high as pressures commonly achieved in pressure cookers at the applicable temperatures.

The length of time during which the Makroot fruit is boiled is not particularly limited, and any time period from about 1 minute to 2 hours may be applied but a time period of from 10 to 20 minutes is preferred. The quantity of water or solution used in comparison with that of the Makroot fruit is not particularly limited as long as there is sufficient water or solution present to prevent scorching of the Makroot fruit. A volume of water ranging between equal to that of the Makroot fruit to about 10 times the volume of the Makroot fruit is preferred. The material of the vessel is not particularly limited and metals, such as stainless steel, ceramics and glasses used in the construction of such vessels may be used.

The manner of sectioning or dividing the fruit is not particularly limited and depends upon the specific embodiment of the NHR method to be used. For manual application the fruit may be cut and pieces having dimensions of about 2 centimeters to a half fruit are preferred. The Makroot fruit may also be diced, cored, ground, crushed, pulverized, or sliced or the like or any combination of these determined to yield extract satisfactory to the embodiment of the NHR method being applied. In the event that the embodiment of the present invention in which the Makroot fruit is boiled is used, there is no limitation as to whether the sectioning or dividing of the Makroot fruit is carried out before or after boiling, but sectioning or dividing the Makroot fruit after boiling is preferred.

In the embodiments of the present invention where an extract is used in place of the boiled Makroot fruit itself, it is preferred that the extraction be accomplished by first removing the rind of the Makroot fruit. The method of removing the rind is not particularly limited but cutting the pulp out is preferred. In the event that the extraction is accomplished by juicing or pressing, the rind may be separated manually or mechanically at the end of the extraction and disposed off. Moreover, it is preferred that the seeds of the Makroot fruit be removed. As with the rind the seeds may be removed when the fruit is sectioned or cut or they may be removed manually or mechanically with the rind during juicing or they may be filtered in those embodiments in which filtration of the extract is carried out.

Then, as one method of extraction of the present invention, the pulp with or without rind and seeds may be juiced, the pulp and seeds removed as stated above and the pulp left with the resulting juice as the extract. In this case the pulp may be either ground and crushed or left as is. Alternatively the mixture of pulp and juice and in some cases seeds or rind may be separated by filtration, settling or centrifugation, in which case only the decanted juice or liquid is used as the extract of the present invention. The extract may be diluted with aqueous solution or water, concentrated by evaporation or otherwise further treated as desired, but the pure extract of the Makroot fruit is preferred.

For those embodiments of the present invention that require it, any of the forms of said extract may be combined with other suitable cosmetic materials to facilitate effective and simple storage and application as creams, solutions, sera, essences, or other such forms. For example, the extract may be combined with thickener, foam booster, stabilizer, antimicrobials, emulsifier, skin conditioners, etc., to obtain a topical cream.

The NHR composition of the present invention is the boiled and sectioned Makroot fruit or the extract of the boiled Makroot fruit comprising the juice of the said boiled Makroot fruit extracted according to the present invention.

The NHR method of the present invention is the application of the NHR composition to white hair at the hair growth sites by any suitable means, and coating the hair growth site, for which the natural hair recoloration and hair growth stimulation effect is desired with the NHR composition, is preferred, and the said application accompanied by manual or mechanical rubbing of the hair growth site is more preferred. For the sake of ensuring low cost application, manual application and rubbing are most preferred. The hair growth sites that may be treated with the NHR method of the present invention are not particularly limited, but scalp and (for men) facial hair are the preferred application sites.

Concretely, the period of application is not particularly limited but to obtain the most effective results a period of application of between about 1 week and 6 weeks is preferred and 3 to 5 weeks is more preferred. The number of applications per week is not particularly limited and a frequency of application of from about 1 application per week to daily applications is preferred and evenly spaced applications 2 or 3 per week are more preferred.

In the direct application embodiment, the boiled Makroot sectioned surfaces are rubbed onto the hair growth sites so that the Makroot juice is applied directly. The quantity of NHR method applied is not particularly limited but should be enough to lightly coat the area to be treated. The length of time this NHR composition is left on the scalp is not particularly limited but a period of from 15 minutes to 1 hour is preferred after which the NHR composition is gently washed away with water.

In the preferred embodiment of the present invention involving application of the extract or derivatives of the extract in cosmetic base, is essentially the same as for the boiled fruit. The amount of the extract to be applied is not particularly limited, and may depend upon the concentration of the extract, and any base in which the extract has been placed, but a quantity that can easily be rubbed onto and lightly but completely cover the area to be treated is preferred. The time period for allowing the extract or derivatives of the extract in cosmetic base is not particularly limited and in the case of the extract in a cosmetic or other base or matrix which is absorbed by the skin, there may in some cases be no need for removal by washing.

The practice examples of the present invention are described below. The examples are for the purpose of demonstrating the practice of the present invention and do not and are in no way intended to limit the scope of the present invention.

EXAMPLES 1-11

An NHR composition was prepared by washing 4 sets of 30 ripe whole Makroot fruits about 5 centimeters in diameter in a dilute aqueous sodium hypochlorite (bleach) solution (100 ml ppm) in 5 liters of water, rinsing them in pure water and then boiling them in 5 liters of water in stainless steel pots at 100° C. for 18 minutes. The water was cooled and disposed of and the Makroot fruits sectioned, the seeds were removed from the sectioned pieces and these pieces were juiced by squeezing using a hand juicer. The resulting pulp and juice mixture was filtered using a fabric squeeze hand filter, and the filtrate was placed in resealable plastic containers, weighed, sealed, cooled in water at 15° C. or less and stored in a refrigerator or refrigerated room at 10° C. or less to obtain the natural hair coloration and hair growth stimulation composition of the present invention. Refer to FIG. 2 for a flow chart of the process of preparing the NHR composition used in the present practice examples.

Eleven men and women whose original hair color was brown or black were selected as experimental subjects, a test period of 4 weeks was selected, and the number of applications set between one and five times per week. The experimental subjects were each provided a supply of the NHR composition and simple instructions to apply sufficient NHR composition directly to the hair growth sites on the scalp where they had white hairs. After applying the NHR composition according to these instructions, observations were made by each experimental subject, as to (1) whether the white hairs at the said hair growth site turned brown or black and (2) whether the hair loss at the said hair growth site decreased or not. Moreover, as other items of observation or investigation, they further recorded (3) whether or not dandruff was prevented at the said hair growth site and (4) whether or not there was itchiness at the said hair growth site were also observed or investigated. The results of the observation or investigation of the aforementioned items (1) through (4) are shown in FIG. 1.

In FIG. 1, 6 among 11 of the experimental subjects responded that their white hair had turned to brown (or turned to black) (Practice Examples 1, 2, 5, 7, 8, 11) and 6 of the experimental subjects responded that their hair loss had decreased (Practice Examples 2, 4 through 7, 10), and, moreover, there were 6 experimental subjects who reported that their dandruff had disappeared (Practice Examples 1, 2, 4 through 6, 9). In addition, although 8 experimental subjects reported no itchiness at their hair growth sites (Practice Examples 2 through 5 and 8 through 11), in none of the 11 experimental subjects did side effects such as inflammation or eczema occur. And further, one experimental subject (Experimental Subject 2) reported that their hair straightened and another experimental subject (Experimental Subject 3) reported increased resilience and body in their hair From these results, it can be clearly understood that by directly rubbing processed Makroot fruit on, or applying the Makroot juice to hair growth sites, it is possible to effectively return white hair in these hair growth sites to their original color and to stimulate hair growth. Moreover, it may be understood that by using the inexpensive Makroot fruit, it is possible to return white hair to its original color and stimulate hair growth at low cost, and, additionally, that it may be used simply without the need for complicated treatments and processes and the like.

Effects of the Present Invention

Using the hair recoloration and agents of the prior art, that require complicated processing and handling through to completion of the final product, no comparatively significant effect of natural hair recoloration has been achieved. Moreover, because small quantities of chemical additive are present in those final products, the user feels the stimulation of the scalp and there are the undesirable side effects of inflammation or eczema may occur.

The embodiments of the present invention overcome these deficiencies because the extracts obtained from the pulp and rind of the Makroot are used as the NHR composition and are applied directly to the hair growth sites without having extracted or dissolved them using synthetic solvents such as ethanol. Consequently, the user feels no stimulation nor suffers any side effects, generally allergy sufferers or persons in delicate health may also use the present invention with confidence.

The invention claimed is:

1. A method for recoloring natural hair by applying to the hair a composition comprising an extract obtained from boiled Makroot fruit for natural hair recoloration.

2. The method according to claim 1 wherein the composition returns the color of white hair to their original color.

3. The method according to claim 1 wherein the composition is applied to the hair growth sites one or more times.

4. The method according to claim 1 wherein the extract of Makroot fruit comprises sectioned boiled Makroot fruit.

5. The method according to claim 1 wherein the extract of Makroot fruit comprises the juice of boiled Makroot fruit.

6. The method according to claim 1 wherein the application of the composition is carried out between two and three times per week for a period of 3 to 6 weeks.

7. The method according to claim 1 wherein the extract is mixed with cosmetic bases and/or other additives.

\* \* \* \* \*